(12) United States Patent
Weitzner et al.

(10) Patent No.: US 8,992,559 B2
(45) Date of Patent: Mar. 31, 2015

(54) GASTRIC FILLER DEVICES FOR OBESITY THERAPY

(75) Inventors: Barry Weitzner, Acton, MA (US); Stephen Moreci, Hopedale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 714 days.

(21) Appl. No.: 13/293,371

(22) Filed: Nov. 10, 2011

(65) Prior Publication Data

US 2012/0053613 A1 Mar. 1, 2012

Related U.S. Application Data

(62) Division of application No. 12/052,293, filed on Mar. 20, 2008, now abandoned.

(60) Provisional application No. 60/910,356, filed on Apr. 5, 2007.

(51) Int. Cl.
*A61M 29/00* (2006.01)
*A61F 5/00* (2006.01)

(52) U.S. Cl.
CPC .............. *A61F 5/0003* (2013.01); *A61F 5/0036* (2013.01)
USPC ........................................................ 606/191

(58) Field of Classification Search
CPC ..... A61F 5/0003; A61F 5/0013; A61F 5/003; A61F 5/0036; A61F 5/0076; A61F 5/0079; A61F 5/0083; A61F 5/0089; A61M 2210/1053; A61F 2/97
USPC ................ 606/191, 192, 195, 198; 623/23.65
See application file for complete search history.

(56) References Cited

U.S. PATENT DOCUMENTS

| | | | | |
|---|---|---|---|---|
| 2,508,690 | A | * | 5/1950 | Fritz ............................. 604/265 |
| 5,545,132 | A | * | 8/1996 | Fagan et al. ............. 604/103.08 |
| 7,004,963 | B2 | * | 2/2006 | Wang et al. ................... 623/1.11 |
| 2002/0055757 | A1 | * | 5/2002 | Torre et al. .................... 606/192 |
| 2005/0192615 | A1 | * | 9/2005 | Torre et al. .................... 606/192 |
| 2007/0198039 | A1 | * | 8/2007 | Jones et al. .................... 606/151 |
| 2007/0239284 | A1 | * | 10/2007 | Skerven et al. ............. 623/23.65 |
| 2008/0249635 | A1 | * | 10/2008 | Weitzner et al. ........... 623/23.65 |

* cited by examiner

*Primary Examiner* — Tuan V Nguyen
*Assistant Examiner* — Christian Knauss
(74) *Attorney, Agent, or Firm* — Fay Kaplun & Marcin, LLP

(57) ABSTRACT

An obesity treatment device comprises a filament filler material movable between a substantially straight insertion/removal configuration and an operative configuration in which the filament extends along a predetermined curve to occupy a selected volume within the stomach and a retrieval device connected to a proximal end of the filler material facilitating grasping and withdrawal of the filler material. A method of treating obesity, comprises inserting to a desired position within the GI tract a filament filler in a substantially straight configuration and moving the filler into an operative configuration in which the filler curves along a predetermined path to define a desired volume in combination with, after a predetermined treatment period has elapsed, collapsing the filler into the substantially straight configuration for trans-oral removal.

20 Claims, 1 Drawing Sheet

GASTRIC FILLER DEVICES FOR OBESITY THERAPY

PRIORITY CLAIM

This application is a Divisional application of U.S. patent application Ser. No. 12/052,293 filed on Mar. 20, 2008, now abandoned, entitled "Gastric Filler Devices for Obesity Therapy", which claims priority to U.S. Provisional Patent Application Ser. No. 60/910,356 filed on Apr. 5, 2007. The entire disclosure of the prior applications is considered as being part of the disclosure of the accompanying application and hereby expressly incorporated by reference herein.

BACKGROUND

The incidence of obesity is rapidly increasing in industrialized countries and methods and procedures to control the weight of obese individuals is receiving ever increasing attention. In addition to diets and other lifestyle changes, aggressive medical procedures are available to limit caloric intake. Many procedures limit the amount of food digested by, for example, blocking or bypassing portions of the gastro intestinal (GI) tract. Other procedures focus on generating feelings of satiety after ingestion of reduced quantities of food.

One such treatment involves placing a filler material within the stomach, often through the esophagus. The filler material takes up room in the stomach, generating a feeling of satiety and reducing the desire to eat. The material also restricts and slows the passage of food through the stomach into the intestines, extending the duration of the feeling of satiety and the reduced desire to eat.

One type of filler includes gas filled bubbles which float upward and apply pressure on the greater curvature of the stomach wall. This pressure is sensed by baro-receptors in the greater curvature which send a signal to the brain indicating that the stomach is full. Fluid filled and other non-floating filling devices apply a downward force to the stomach wall which also generates feelings of satiety.

SUMMARY OF THE INVENTION

The present invention is directed to a gastric fill device comprising a conduit having a lumen with a distal end insertable in the stomach and a proximal end accessible externally, a filler material having a substantially straight string-like configuration used for insertion and for removal from the stomach, and an expanded operative configuration to occupy a selected volume within the stomach, and a retrieval element operatively connected to the filler material for grasping and withdrawing the filler material.

In another aspect, the present invention is directed to an obesity treatment device comprising filament filler material movable between a substantially straight insertion/removal configuration and an operative configuration in which the filament extends along one or more curves to occupy a selected volume within the stomach and a retrieval element connected to a proximal end of the filler material facilitating grasping and withdrawal of the filler material.

The present invention is further directed to a method of treating obesity comprising inserting to a desired position within the GI tract a filament filler in a substantially straight configuration and moving the filler into an operative configuration in which the filler curves to define a desired volume in combination with, after a predetermined treatment period has elapsed, collapsing the filler into the substantially straight configuration for trans-oral removal.

DETAILED DESCRIPTION

Figure 1:
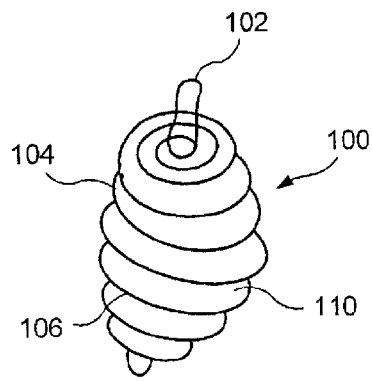
FIG. 1 shows a diagram of a first embodiment of a gastric filler according to the invention.

The present invention may be further understood with reference to the following description and to the appended drawings, wherein like elements are referred to with the same reference numerals. The present invention relates to devices and methods for treating obesity specifically, by partially filling a gastric space. More specifically, the present invention relates to the insertion and removal of gastric space filling devices which has previously proven difficult.

The methods and devices according to the present invention provide devices and methods for more easily deploying and removing space filling devices from the stomach and the upper GI tract. That is, after a predetermined time period has elapsed during which physical limiting of caloric intake is desired, it is preferable to remove the gastric filler from the stomach. However, removal of known gastric fillers has proven difficult for a variety of reasons. Embodiments according to the invention also provide novel space filling technologies and products that may be used as gastric fillers or as fillers in other body spaces designed to facilitate the insertion and removal procedures.

An exemplary gastric filler according to a first embodiment of the invention includes a gastric bubble formed with an integrated deflation and retrieval mechanism simplifying removal of the bubble after the desired treatment period has elapsed. The gastric bubble comprises a shell-like body formed of a polymeric wall including a failure zone preformed in the wall during a molding or other manufacturing operation as, for example, a weakening groove or indentation. The body may be a single filling volume or a series of filling volumes that are either independently or simultaneously fillable. As will be described in more detail below, during removal, the wall is torn along the weakening groove by the removal force, such that the balloon unwinds into an elongated strip that can be easily removed trans-orally. The gastric bubble may be inflated through a self sealing valve mechanism that seals itself when an inflation device (e.g., an inflation tube or catheter) is withdrawn from the valve. The valve may comprise any self sealing valve known to those skilled in the art, such as a basketball valve, a duckbill valve, etc. The bubble may be inflated using air or, alternatively, an inert gas or mixture of gases of predetermined density. In another embodiment, the bubble may be self expanded through a chemical and/or physical reaction with contents of the stomach. For example, the bubble may be inserted in an unexpanded state and upon delivery, may enter an expanded state by absorbing stomach fluids.

FIG. 1 shows an exemplary embodiment of a gastric balloon 100 including an outer wall 104 with a failure zone formed as a groove 106 extending around the wall 104 in a spiral. Those skilled in the art will understand that the failure zone is formed so that a strength of the wall 104 in this area is reduced with respect to the rest of the wall 104 (e.g., by thinning this portion of the wall) so that, when subject to a predetermined stress, the wall 104 will separate along the groove 106. A tag with a loop 102, or other retrieval element, is connected to one end of the gastric balloon 100 so that it may be grasped and pulled by the physician with a grasping instrument, for example, under direct visualization using an endoscope to apply the predetermined stress to the failure zone. When it is desired to remove the gastric balloon 100 from a portion of the GI tract into which it has been inserted, the user locates the tag 102 (e.g., under direct visualization via an endoscope) and manipulates a grasping device to apply tension to the balloon 100 to cause an initial break of the material forming the wall 104 along the groove 106. As the application of tension is continued, the wall 104 unravels into a long piece of tape 110 which is removed as the grasping device is withdrawn through the esophagus and the mouth or which is drawn with the grasping device into the working channel of the endoscope which is then withdrawn transorally. In the exemplary embodiment shown in FIG. 1, the balloon 100 has a substantially spherical shape. However, other embodiments may include other geometries, such as cones, cylinders, elliptical shapes, etc.

Figure 2:
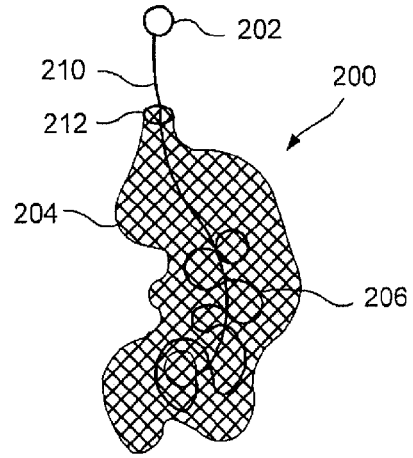
FIG. 2 shows a second embodiment of a gastric filler according to the invention.

As shown in FIG. 2, a gastric balloon 200 according to a second embodiment of the invention includes a net or bag 204 which, after insertion into a desired portion of the GI tract (e.g., the stomach), is filled with a filler material until the balloon 200 takes up a desired volume. The filler material preferably comprises string or a similar material easily inserted into and removed from the GI tract via the mouth. The net 204 includes a tether end 202 which is coupled to the filler material to facilitate grasping by a retrieval device inserted via an endoscope for removal of the filler material from the body. The net 204 may be formed as a porous netting or a fluid/gas barrier depending on a degree of desired interactivity between the stomach contents and the balloon 200. A higher degree of porosity may result in faster transport of materials through the stomach while a lower porosity may impede material transport. The net 204 may include one or more preformed failure zones. For example, the net 204 may be woven or crocheted so as to unravel when pulled. In some embodiments, portions of the net 204 and/or the filler material may be biodegradable or dissolvable. For instance, the net 204 may be dissolvable by application of a solvent, a dissolving solution or heat, or may be designed to dissolve after a predetermined period of time after exposure to stomach fluids (e.g., three months). Once the net 204 is dissolved or manually broken, the filler material may be exposed to the same or another dissolving agent, and may be absorbed or passed through the digestive system.

The filler material in this exemplary filler balloon 200 is formed as a length of string 206 coupled to the tether end 202. The string 206 is inserted into the net 204 via an opening 212 after the bag 204 has been placed in the stomach or other desired location within the GI tract. As an alternative to or in addition to the string 206, other filler materials, such as hydrogels, beads, absorbable elements, etc., may be used to give the desired volume to the net 204. The filler material may also have a specified geometry that facilitates deployment, filling or removal of the balloon 200. Exemplary geometries include dimpled or porous surfaces and variable sized or shaped elements.

Both the string 206 and the bag net 204 may be inserted using endoscopic instruments and procedures allowing the trans-oral insertion and removal of these gastric filling devices to be accomplished easily and rapidly. As described above, the string-like filler material may be grasped at one end, such as by an end 210 attached to the tether 202, and pulled out through the esophagus and the mouth. The bag or net 204, once deflated by removing the filler material, may then be pulled out through the esophagus and mouth in the same manner described above for the string-like filler material. The string 206 may also be coupled to the bag 204 to facilitate removal of the bag 204 after the string 206 is removed. Thus, removal of both the string 206 and the bag 204 may be performed in a single step. In another embodiment, the tether 202 may comprise a ripcord coupled to the bag 204. That is, the tether 202 may perform a tearing or opening function. In an embodiment where the bag 204 comprises multiple filling volumes, the tether 202 may separate the multiple volumes and/or individually open or tear each volume separately as would be understood by those skilled in the art.

In a different embodiment according to the invention, the gastric fill material comprises a stand-alone filling device placed within the stomach without a constraining element such as a net or a bag. The filling device may comprise any shape that provides a desired filling characteristic. For example, the filling device may be shaped to fill a portion of the antrum (e.g., tapered, conical, etc.), thereby slowing gastric emptying. Exemplary filling device shapes include open coils, S-ribbons, stars, shapes with wide and/or irregular cross-sections, etc. The filling device may be formed of any biocompatible elastic material, such as stainless steel, platinum, titanium, a polymer, etc. In another embodiment, the filling device may comprise a shape memory material such as Nitinol and other materials used in the manufacture of embolic coils for treating aneurysms. The filling device may be inserted or removed through a working channel of an endoscope/delivery tube in a substantially low profile and deformed using any combination of mechanical, electrical or chemical techniques. Alternatively, the filling device may be delivered while wrapped around an exterior of the endoscope/delivery tube. In some embodiments, the filling device may be deformed using electricity, temperature change, a physical or chemical reaction (e.g., absorption of fluids), manual manipulation, etc. The deformation may be in multiple dimensions (e.g., three-dimensional expansion, two-dimensional torsion, etc.). In some embodiments, the deformation may be reversible so that the filling device may be withdrawn while maintaining the low profile.

In another embodiment, the stand-alone filling device may be formed of an interwoven material comprising a three-dimensional mesh or nest. A weaving pattern may be selected to facilitate insertion and removal of the filling device, or to regulate the transport of material through the stomach. The mesh may be woven into any number of shapes, such as those described above with reference to the stand-alone device (e.g., cones, stars, irregular patterns, curved patterns, etc.).

Figure 3:
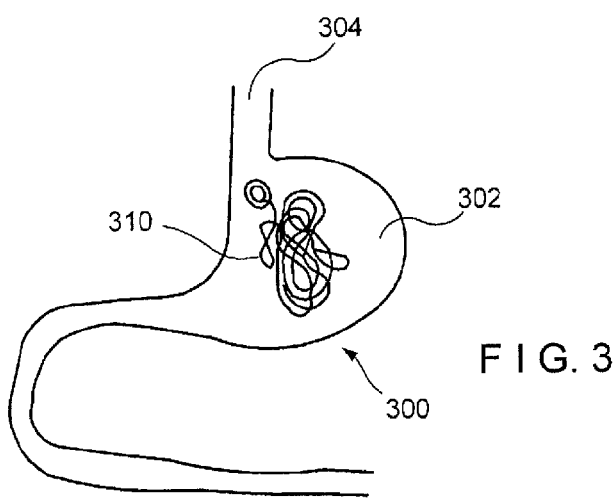
FIG. 3 shows a diagram of a third embodiment of a gastric filler placed within the stomach.

FIG. 3 shows an exemplary embodiment of a gastric filling device 300 comprising a coil 310 which is deployed into the stomach 302 via an endoscope or other tubular device inserted through the mouth and esophagus 304. The lower esophageal sphincter ("LES") and the esophagus 304 are protected from damage or irritation by maintaining the coil 310 within the working channel of an endoscope during insertion and removal of the coil 310 therethrough. Additionally, some patients may have feeding tubes, such as a percutaneous endoscopic gastrostomy (PEG) tube placed through an oral cavity or percutaneously (e.g., through an abdominal stoma). In such instances, the feeding tube may function as a delivery and/or removal device for the filling device 300.

The coil 310 may be formed of a shape memory material. As would be understood by those skilled in the art, the shape memory properties of the coil 310 allow the coil 310 to be maintained in a substantially straight shape during insertion through the working channel of the endoscope with the material reverting to a memorized coil shape after deployment within the stomach 302. Thus, the substantially straight shape facilitates trans-oral insertion while the shape memory properties of the coil 310 allow it to expand to a pre-selected shape and volume without the need for a separate constraining device such as the bag, net or bubbles described above. As with the above-described embodiments, the operative shape and volume are selected so that, when in a desired position within the stomach 302, the volume taken and/or the stimulation applied to the wall of the stomach 302 enhances feelings of satiety. For example, the material of the coil 310 may be formed to take the form of a sphere or other hollow shell geometry after it has been deployed in the stomach 302. After completion of the treatment, the coil 310 may be returned to its substantially straight shape to be removed by, for example, grasping a proximal end of the coil 310 and drawing the coil into the working channel of an endoscope. The force of pulling into the endoscope causes the coil 310 to straighten. Alternatively, in other embodiments, the shape change may be caused by a stimulus such as an electrical signal, a chemical or physical reaction (e.g., absorption of fluid), etc.

In another embodiment, the coil 310 may be formed of an elastic material without shape memory, but with sufficient malleability so as to retain shape after being manually deformed. Alternatively, the elastic material may be biased towards the straight, low profile configuration, deforming to accommodate a natural curvature of the stomach wall.

The embodiments of the gastric filler according to the invention described above may be deployed and retrieved using conventional techniques, such as endoscopic procedures. However, improved devices to manipulate the gastric filling devices are within the scope of the invention. The improved methods and devices may be used in conjunction with the gastric filling devices described above, as well as with conventional gastric balloons and bubbles used for the treatment of obesity.

In one exemplary embodiment, access to the stomach of a patient may be provided by a catheter placed through the esophagus. A stent-like device is inserted through the catheter trans-orally in a compact configuration, such as folded unto itself. Once placed in the stomach, the device opens up like a stent, and takes up a selected volume within the stomach. This gives to the patient a feeling of satiety or fullness, so that less food is ingested. For example, the catheter may be a AAA stent-graft marketed by Trivascular and Boston Scientific Corporation, of Natick, Mass. The stent may comprise any number of shapes, including a cylinder, a ball and a torpedo. The stent is free floating in the stomach and may be sized to produce a desired amount of satiety.

In another exemplary embodiment, the delivery and retrieval system used for a gastric filling device utilizes a flexible overtube inserted into the GI tract and advanced until a distal end reaches a desired position within the stomach. At this point, a shape of the overtube may be locked so that forces applied to the overtube via devices inserted and/or withdrawn therethrough are absorbed by the overtube itself without being transferred to the surrounding tissue. Alternatively, the overtube may remain in an unlocked, flexible configuration so long as the overtube is maintained in the desired position.

Figure 4:
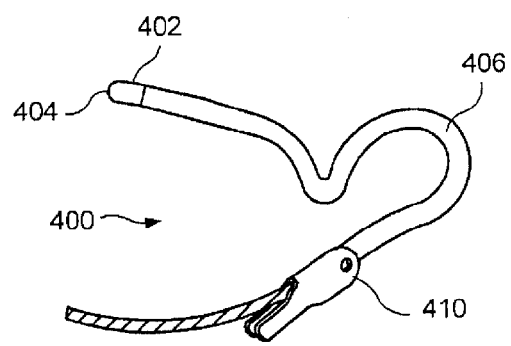
FIG. 4 shows an embodiment of a delivery and retrieval system for a gastric filler according to the invention.

As shown in FIG. 4, an exemplary locking overtube 400 includes a distal end 402 which is inserted trans-orally through the esophagus into the stomach. The overtube 400 comprises a lumen 404 extending its entire length to an opening formed in the distal end 402. A liner is passed through the lumen 404 and out of the opening in the distal end 404 to provide access to the stomach. The body 406 of the overtube 400 has a flexible configuration in which it is free to bend and change shape to simplify insertion through the GI tract. The shape locking mechanism may consist of a series of nested rings linked together via one or more cables and locked into position by tightening the cables. The overtube 400 includes a controller 410 actuated by the user to change the configuration of the body 406 between the locked and flexible configurations. In the locked configuration the overtube 400 withstands torsional and axial loads (e.g., those applied thereto as instruments are inserted through and withdrawn from the lumen) without changing shape. The locked overtube 400 provides a stable platform through which the gastric filling material may be inserted or removed, as the locked configuration maintains the distal end 402 in a substantially constant position within the stomach as forces are applied therethrough to remove the filler material.

Alternatively, an overtube for use in conjunction with the invention may include all of the elements of the includes overtube 400 except for the shape locking mechanism and controller described to provide a passive, stable platform through which the gastric filling material may be inserted or removed.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. An obesity treatment device, comprising:
   a hollow bubble having a shape that is one of substantially spherical and substantially ovoid, in an insertion/removal configuration, the bubble sized to be slidably inserted through the esophagus and, in an operative configuration, the bubble configured to be inflated to a desired volume within a stomach, the bubble including a flexible outer wall and a failure zone formed in the wall so that, when the bubble is subject to a predetermined stress, the wall fails along the failure zone, wherein the failure zone is formed as a spiral groove weakened with respect to other portions of the wall and directs tearing of the wall into an elongated tape; and
   a handle being operatively connected to a proximal end of the outer wall facilitating grasping and retrieval of the wall to draw the wall proximally.

2. The device of claim 1, wherein the handle is aligned with the failure zone so that proximally directed force applied to the handle causes the wall to unwind along the failure zone.

3. The device of claim 1, wherein the failure zone is configured so that, after being torn therealong, the wall is sized for trans-oral withdrawal.

4. The device of claim 1, wherein the failure zone is formed via a thinning of the wall therealong.

5. The device of claim 1, wherein the handle includes a tag and loop which, when grasped and drawn proximally causes a break in the wall along the groove.

6. The device of claim 1, wherein the bubble is configured to be one of inflated via air and self expanding.

7. A gastric fill method, comprising steps of:
   inserting into the stomach a bubble including a failure zone formed in a wall thereof such that, upon application of a proximally directed retrieving force, the wall to tears along the failure zone;

inflating the bubble to a desired volume;

after a desired treatment period has elapsed, applying the retrieving force to the bubble, tearing the wall, wherein the failure zone is formed as a spiral groove weaker than other portions of the wall, such that when torn along the failure zone, the wall unravels to form an elongated strip; and retrieving the elongated strip trans-orally.

8. The method of claim 7, wherein inserting and removing the bubble is performed using one of a flexible and a shape lock overtube.

9. The method of claim 7, wherein the retrieval force is applied to the bubble via an endoscopically inserted grasping device.

10. The method of claim 7, wherein the failure zone is formed via a thinning of the wall therealong.

11. The method of claim 7, wherein the bubble further includes a retrieval element connected to an end of the bubble so that, when the retrieving force is applied thereto, the wall unravels to form the elongated strip.

12. The method of claim 11, wherein the retrieval element is a tag and loop which, when grasped and drawn proximally causes a break in the wall along the groove.

13. The method of claim 11, further comprising locating the retrieval element using direct visualization via an endoscope.

14. A device for treating obesity, comprising:
a hollow balloon sized to be slidably inserted through the esophagus into the stomach in an insertion configuration, the balloon configured to be inflated to a desired volume within the stomach in an operative configuration;
a failure zone formed along a flexible outer wall of the balloon so that, when the balloon is subject to a predetermined stress, the wall fails along the failure zone, wherein the failure zone is formed as a spiral groove weakened with respect to other portions of the wall and directs tearing of the wall into an elongated tape for removal of the device from the stomach; and
a retrieval element connected to an end of the wall of the balloon so that, when a retrieving force is applied thereto, the wall tears along the spiral groove.

15. The device of claim 14, wherein the elongated tape is sized and shaped for trans-oral withdrawal.

16. The device of claim 14, wherein the retrieval element is configured to be grasped via a grasping device.

17. The device of claim 14, wherein the retrieval element is a tag and loop connected to the proximal end of the balloon.

18. The device of claim 14, wherein the spiral groove is formed via a thinning of the wall therealong.

19. The device of claim 14, wherein the balloon is one of substantially spherical, conical, cylindrical and elliptical.

20. The device of claim 14, wherein the balloon is configured to be one of inflated via air and self-expanding.

* * * * *